United States Patent [19]

Ko et al.

[11] Patent Number: 4,877,037
[45] Date of Patent: Oct. 31, 1989

[54] TISSUE OR MUCUS SAMPLING DEVICE

[75] Inventors: Su-sen Ko; Dan L. Fanselow, both of White Bear Township, Ramsey County, Minn.

[73] Assignee: Minnesota Mining and Manufacturing Company, St. Paul, Minn.

[21] Appl. No.: 254,358

[22] Filed: Oct. 6, 1988

Related U.S. Application Data

[63] Continuation-in-part of Ser. No. 69,766, Jul. 6, 1987, abandoned, which is a continuation-in-part of Ser. No. 796,967, Nov. 12, 1985, abandoned.

[51] Int. Cl.⁴ .............................................. A61B 10/00
[52] U.S. Cl. ..................................... 128/756; 128/757; 128/759; 128/768; 604/55; 604/117; 604/164
[58] Field of Search ............... 128/749, 750, 756, 757, 128/759, 768; 604/40–42, 54, 55, 117, 164–171

[56] References Cited

U.S. PATENT DOCUMENTS

| | | | |
|---|---|---|---|
| 3,592,186 | 7/1971 | Oster | 128/2 R |
| 3,640,268 | 2/1972 | Davis | 128/759 |
| 3,664,328 | 5/1972 | Moyle, Jr. et al. | 128/2 B |
| 3,776,219 | 12/1973 | Brown | 128/2 B |
| 3,877,464 | 4/1975 | Vermes | 128/759 |
| 3,961,620 | 6/1976 | Schack et al. | 128/757 |
| 4,067,323 | 1/1978 | Troutner et al. | 128/18 |
| 4,131,112 | 12/1978 | Kopite et al. | 128/2 B |
| 4,136,680 | 1/1979 | Southworth | 128/213 |
| 4,157,709 | 6/1979 | Schuster | 128/759 |
| 4,318,414 | 3/1982 | Schuster et al. | 128/759 |
| 4,324,262 | 4/1982 | Hall | 128/756 |
| 4,485,824 | 12/1984 | Koll | 128/756 |
| 4,493,700 | 1/1985 | Casson et al. | 604/55 |
| 4,534,362 | 8/1985 | Schumacher et al. | 128/738 |
| 4,562,847 | 1/1986 | Nydahl et al. | 128/757 |

FOREIGN PATENT DOCUMENTS

| | | | |
|---|---|---|---|
| 1394925 | 5/1975 | Brazil. | |
| 2126100 | 3/1984 | United Kingdom | 128/749 |

Primary Examiner—Max Hindenburg
Assistant Examiner—Randy Citrin
Attorney, Agent, or Firm—Donald M. Sell; Walter N. Kirn; Dale A. Bjorkman

[57] ABSTRACT

An extremely simple cervical tissue or mucus sampling device comprising an outer protective sleeve, a guard means, a telescoping insertion tube, a stop means and a tissue or mucus sampling member is disclosed which enables a woman to obtain a sample of cervical tissue or mucus for examination and testing.

14 Claims, 2 Drawing Sheets

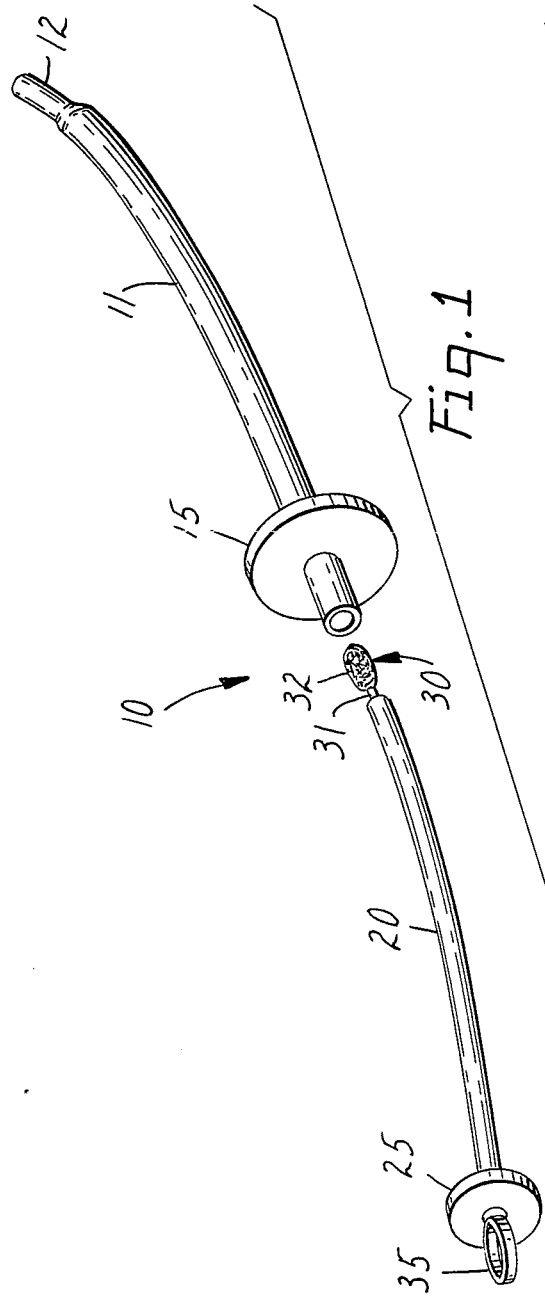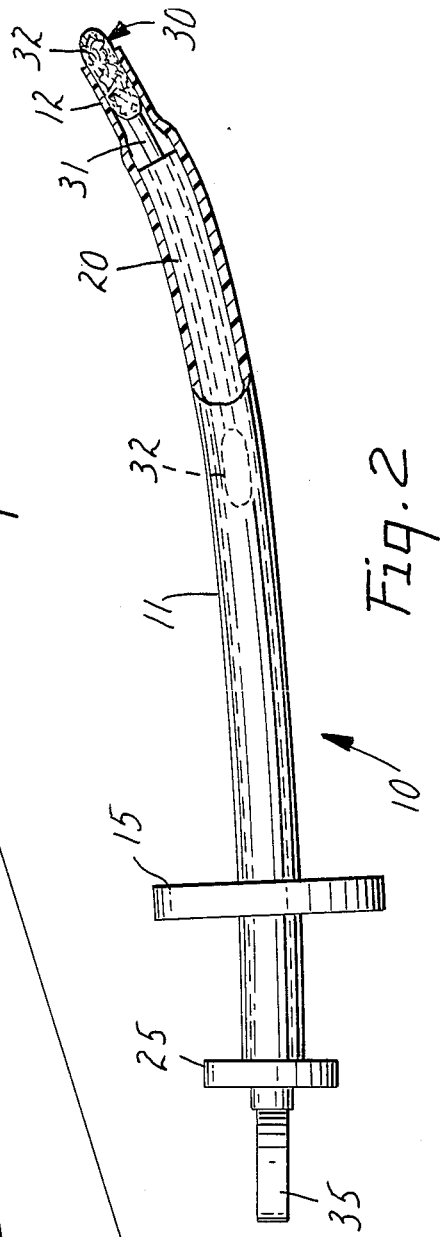

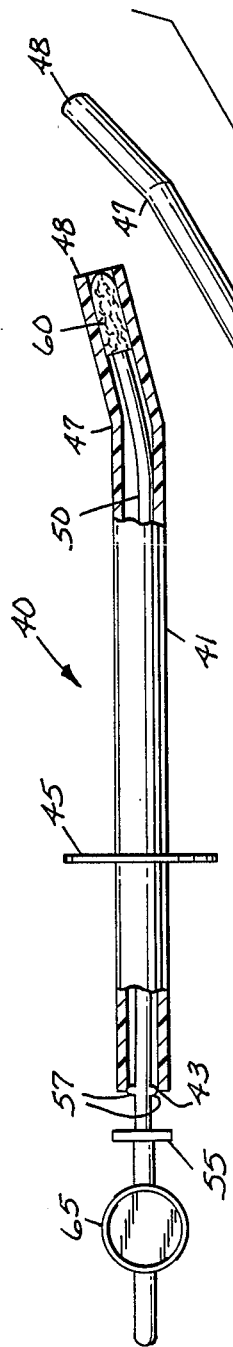
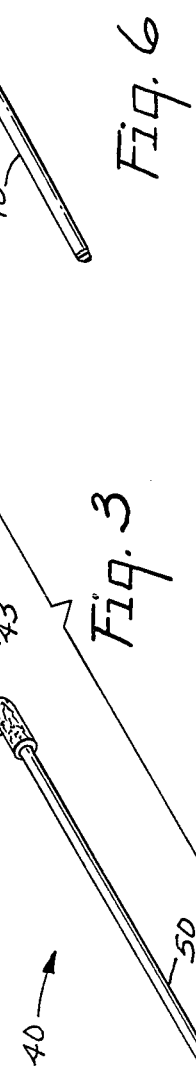
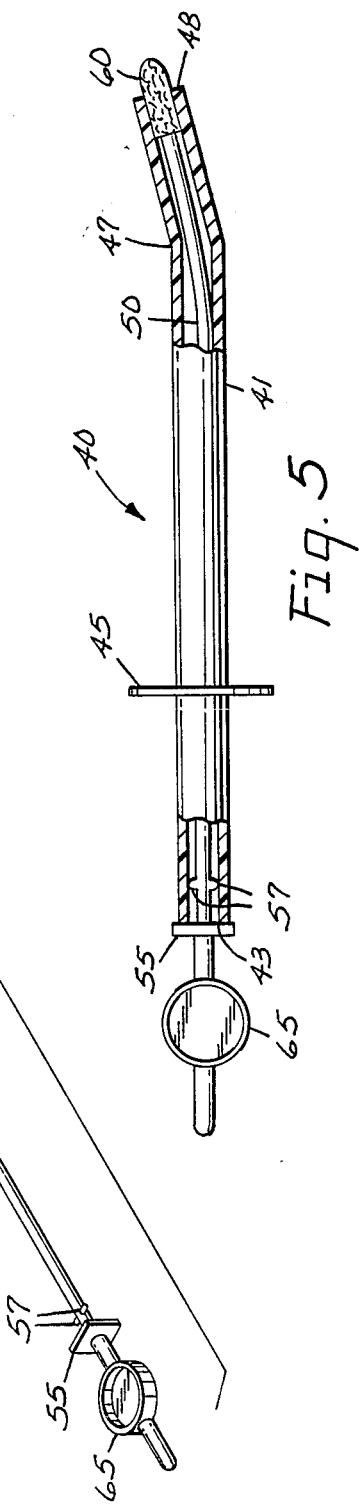

TISSUE OR MUCUS SAMPLING DEVICE

This application is a continuation-in-part of application Ser. No. 069,766, filed July 6, 1987, abandoned which is a continuation-in-part of application Ser. No. 796,967, filed Nov. 12, 1985, abandoned.

BACKGROUND OF THE INVENTION

The present invention relates to a sampling device for obtaining a tissue or mucus sample from the cervical os or from the upper region of the vagina (vaginal fornix) without undue contamination of the sample by vaginal fluids.

Collection of cervical material in the form of tissue and mucus has been routinely performed for many years. Such retrieved samples are then tested for malignancy by the Pap test or examined for various purposes such as the determine whether ovulation has occurred.

The probes or devices generally used to obtain such cervical samples for examination and testing have not been designed for self-use by women wishing to collect cervical specimens at home. In most instances, skilled medical personnel obtain the required sample for testing. Some recent patents disclose sampling devices designed specifically for self-use by women.

U.S. Pat. No. 3,592,186 relates to an apparatus for self-use in the collection of cervical samples for evaluation. The apparatus comprises a substantially resilient scraper having a generally irregular heart-shape telescopically engaged within a protective cover. When the apparatus is disposed substantially within the female body at the vaginal opening, the scraper is extensible and rotatable by the individual from whom the sample is to be obtained. An indexer is provided to give external indication to the operator of the relative position of the scraper when in operation.

U.S. Pat. No. 3,776,219 discloses a cervical scraper unit designed particularly for utilization by the female herself. The scraper comprises a conical polyurethane foam head cantilevered at the end of a hollow plastic tube and enveloped by a plurality of protective flexible petal-like appendages. The head is mounted to be exposed by the petals at the testing site, and to accommodate its collapse and flexion when it is rotated in situ against the entrance to the cervix. Subsequently, the petals are arranged to envelop and protect the head during withdrawal. The ability of the scraper to collapse and to flex, its resilient nature, and its conical shape, along with the protection of the sample by the petals, are all said to contribute to the efficiency and completeness of transfer of a collected sample for examination.

U.S. Pat. No. 4,131,112 provides a probe for obtaining a sample of cervical mucus which comprises a syringe-like structure characterized by an outer barrel and an inner plunger capable of producing relative peristaltic motion. The cooperating forward configurations of the outer barrel and the inner plunger defines therebetween the specimen cavity which, when it is caused to increase in volume with rearward motion of the plunger, receives a fluid specimen through the forward opening under suction and when it is caused to decrease in volume with forward motion of the plunger, ejects the fluid specimen through the forward opening under pressure.

U.S. Pat. Nos. 4,157,709 and 4,318,414 disclose probes for inserting a test element into the vaginal cavity while shielding it from intermediate vaginal contact, for positioning the test element in contact with the cervical os with the aid of a reference foot, in order to collect a specimen of cervical material and for retrieving the test element and the specimen from the vaginal cavity while shielding them from intermediate vaginal contact.

Other devices for collecting samples of cellular cervical material are disclosed in U.S. Pat. Nos. 3,640,268 and 3,664,328.

SUMMARY OF THE INVENTION

The present invention relates to an extremely simple reusable tissue or mucus sampling device which enables a woman to obtain a sample of tissue or mucus from the cervical os or from the vaginal fornix for examination and testing.

The device comprises an outer protective sleeve, a guard ring on the protective sleeve to provide the user with a guide for proper depth of insertion and a telescoping insertion tube frictionally carrying a swab or scraper for collecting the sample. The device is extremely simple in design and easy to use.

BRIEF DESCRIPTION OF THE DRAWINGS

FIG. 1 is a perspective view of the device of the present invention in an unassembled position;

FIG. 2 is a side view, partly in section, of the device of FIG. 1 in its "in use" position;

FIG. 3 is a perspective view of an embodiment of the device of the present invention in an unassembled position;

FIG. 4 is a side view, partly in section, of the device of FIG. 3 in its "insertion" position;

FIG. 5 is a side view, partly in section, of the device of FIG. 3 in its "collection" position; and FIG. 6 is a partial perspective view of an insertion tube having a scraper as the tissue or mucus sampling member.

DETAILED DESCRIPTION OF THE INVENTION

Referring now to the drawings, tissue or mucus sampling device 10 comprises an outer protective sleeve 11, a guard means 15, a telescoping insertion tube 20, a stop means 25 and a tissue or mucus sampling member 30.

As used throughout the specification, the term "cervical" when used to refer to a mucus sample should be understood to include a mucus sample obtained from the upper region of the vagina (the vaginal fornix).

Protective sleeve 11 is a one-piece elongate cylinder or tube formed of any material of relatively low liquid absorbency with a low coefficient of friction and non-irritating to the human skin, such as stainless steel. Preferably, protective sleeve 41 is formed of a semi-rigid polymer, such as polyvinyl chloride, polypropylene, polyethylene, polyethylene terephthalate, polycarbonate, Teflon or Nylon. The protective sleeve 11 preferably is inclined from the horizontal at an angle of from 15° to 45°. In the case of a protective sleeve 11 formed of a preferred material as described above, this angle may be imparted by thermal treatment. Inclination of tip 12 from the horizontal facilitates the process of obtaining a sample either from the cervical os or from the vaginal fornix due to the anatomy of the cervix relative to the vaginal cavity. In the thermal treatment process, sleeve 11 is drawn so that sleeve 11 is gently tapered along its length and top 12 has a greatly reduced diameter, as clearly seen in the drawings. The resulting reduced diameter of tip 12 assists in minimizing contamination of the cervical mucus sample with vaginal fluids particularly during insertion of the device 10. Protective sleeve 11 can also be injection molded into the desired configuration. It will be appreciated that protective sleeve 11 can also be a straight cylinder or tube with only the tip portion inclined at the desired angle and such an arrangement is contemplated.

Guard means 15, formed of a suitable polymeric material, is tightly frictionally fitted onto protective sleeve 11 for sliding movement therealong. Since guard means 15 functions to limit the depth of insertion of device 10 into the vaginal cavity, the sliding movement of guard means 15 on sleeve 11 is accomplished only with some effort.

Insertion tube 20 is an elongate cylinder or tube formed of any of the same materials as protective sleeve 11, or alternatively is formed of a different material that is sufficiently resilient to be insertable through protective sleeve 11, such as polystyrene or paper. When insertion tube 20 is formed of an absorbant material, it should be discarded after use. As shown in the drawings, insertion tube 20 has an outer diameter slightly smaller than the inner diameter of protective sleeve 11 to permit it to telescopically fit and slide within protective sleeve 11. Insertion tube 20 can, of course, be in the form of a rod.

Stop means 25, preferably formed of a suitable polymeric material, is also tightly frictionally fitted onto insertion tube 20 in like manner as guard ring 15 on protective sleeve 11. Stop means 25 serves to limit the degree of protrusion from tip 12 of the cervical tissue or mucus sampling member 30. Stop means 25 may also be integrally formed as an integral part of insertion tube 20 particularly when insertion tube 20 is in rod form.

As will be seen in FIG. 2, cervical tissue or mucus sampling member 30 is illustrated as a double-ended swab comprising an elongate semi-rigid rod 31, the ends of which are covered with a flexible, soft, resilient fibrous material such as cotton, rayon, polyester or calcium alginate, forming specimen collecting tips 32. It has also been found that foam materials, particularly open cell foam materials, are highly efficient as sampling member 30. Only one of tips 32 is used for collecting a mucus sample. The other tip 32 serves to frictionally hold sampling member 30 firmly in the interior of insertion tube 20. It will be readily apparent to the reader that the end of sampling member 30 inserted into insertion tube 20 can take other forms than shown, e.g., the rod 31 can be of a larger diameter or an elastomeric collar can be placed over the rod end. When sampling member 30 is to be used to collect a tissue sample, the tip of sampling member would be in the form of a scraper.

A handle member 35, shown as a ring, is affixed to one end of insertion tube 20 and is used to guide insertion tube 20 into protective sleeve 11 and also to manipulate the sampling member 30 in insertion tube 20 during use of device 10.

After assembling device 10 by fitting a sampling member 30 into insertion tube 20 and placing insertion tube 20 into protective sleeve 11, stop means 25 is moved along insertion tube 20 so that the tip 32 of sampling member 30 protrudes only slightly from tip 12. Insertion tube 20 is then withdrawn a short distance (approximately one-half to one inch) to avoid contamination of tip 32 with vaginal fluids. Device 10 is then inserted into the vaginal cavity until tip 12 contacts the cervical os. Guard means 15 is then moved into contact with the vaginal orifice to prevent further insertion of device 10 into the vaginal cavity to avoid possible injury to the user. Of course, if device 10 has previously been used for collecting a cervical sample, guard means 15 would already be in the desired position on protective sleeve 11. Insertion tube 20 is then pushed forwardly into protective sleeve 11 by handle member 35 until tip 32 of sampling member 30 is in the predetermined "in use" position shown in FIG. 2. Handle member 35 can then be gently rotated to thus collect a mucus sample. Insertion tube 20 is retracted a short distance and device 10 is then withdrawn. Protective sleeve 11 shields the insertion tube 20 and particularly tip 32 of sampling member 30 during the entire insertion and removal process. Insertion tube 20 is completely withdrawn from protective sleeve 11 and the collected mucus sample is available for further processing for examination and testing.

After each use, device 10 is completely cleaned by washing with soap and water and is ready for reuse. Sampling member 30, if the mucus collecting swab was used is discarded; if a scraper form was used, it is also washed for reuse.

FIGS. 3, 4 and 5 show an alternative embodiment of the tissue or mucus sampling device of this invention 40, comprising an outer protective sleeve 41, a guard means 45, an insertion tube 50, a stop means 55, a surmountable stop means 57, and a tissue or mucus sampling member 60.

Protective sleeve 41 is a one-piece elongate cylinder or tube formed of any material of relatively low liquid absorbency with a low coefficient of friction and non-irritating to the human skin, such as stainless steel. Preferably, protective sleeve 41 is formed of a semi-rigid polymer, such as polyvinyl chloride, polypropylene, polyethylene, polyethylene terephthalate, polycarbonate, Teflon or Nylon. The protective sleeve 41 preferably is angled beginning at a position 47 which is located at about one fifth of the length of the sleeve 41 from the tip 48, so that the tip 48 is inclined from the horizontal at an angle of from 15° to 45°. In the case of a protective sleeve 41 formed of a preferred material as described above, this angle may be imparted by thermal treatment. Most preferably, this angle is 22.5°. Inclination of tip 48 from the horizontal facilitates the process of obtaining a sample either from the cervical os or from the vaginal fornix due to the anatomy of the cervix relative to the vaginal cavity. Protective sleeve 41 can also be injection molded into the desired configuration.

Guard means 45, formed of a suitable polymeric material, is tightly frictionally fitted onto protective sleeve 41 for sliding movement therealong. Since guard means 45 functions to limit the depth of insertion of device 40 into the vaginal cavity, the sliding movement of guard means 45 on sleeve 41 is accomplished only with some effort.

Insertion tube 50 is an elongate cylinder or tube formed of any of the same materials as protective sleeve 41, or alternatively is formed of a different material that is sufficiently resilient to be insertable through protective sleeve 41, such as polystyrene or paper. When insertion tube 50 is formed of an absorbant material, it should be discarded after use. As shon in the drawings, insertion tube 50 is in the form of a rod. Insertion tube 50 can be in the form of a sleeve having an outer diameter slightly smaller than the inner diameter of protective sleeve 41 to permit it to telescopically fit and slide within protective sleeve 41.

Stop means 55, preferably formed of a suitable polymeric material, is integrally formed with the insertion tube 50. Alternatively, the stop means 55 may be provided as a separate piece which is tightly frictionally fitted onto insertion tube 50 in like manner as guard means 45 on protective sleeve 41. Stop means 55 serves to limit the degree of protrusion from the tip 48 of protective sleeve 41.

Tissue or mucus sampling member 60 is located at the first end of the insertion tube 50. Tissue or mucus sampling member 60 is illustrated as a specimen collection tip made of a flexible, soft, resilient fibrous material such as cotton, rayon, polyester or calcium alginate. It has also been found that foam materials, particularly open cell foam materials, are highly efficient as tissue or mucus sampling member 60.

When tissue or mucus sampling member 60 is to be used to collect a tissue sample, the tip of tissue or mucus sampling member 60 would be in the form of a scraper.

A handle member 65, shown as a disk, is affixed to the second end of insertion tube 50 and is used to guide insertion tube 50 into protective sleeve 41 and also to manipulate the sampling member 60 in insertion tube 50 during use of device 40.

Surmountable stop means 57 is provided on insertion tube 50 at a position a distance from the end of tissue or mucus sampling member 60 which is less than or about the same as the length of protective sleeve 41. Surmountable stop means 57 temporarily inhibits the first end of insertion tube 50 from protruding through protective sleeve 41, thereby preventing the protrusion of tissue or mucus sampling member 60 beyond protective sleeve 41 during insertion of collecting device 40 in the vagina. If tissue or mucus sampling member 60 is not shielded, it will pick up mucus from the wrong part of the vagina. It is important that mucus be sampled only in the region of the cervical os in order to provide an effective ovulation indicator.

As shown in the drawings, surmountable stop means 57 is in the form of two protruberances, or "bumps", of material of the same manufacture as insertion tube 50, one bump on either side of insertion tube 50. Surmountable stop means 57 alternatively can be in the form of a widening of insertion tube 50, a ridge, a key and keyhole mechanism wherein tabs on insertion tube 50 must be aligned with slots in protective sleeve 41 to allow further insertion of insertion tube 50 through protective sleeve 41, or any other means which would provide a temporary stop in the insertion of insertion tube 50 into protective sleeve 41. "Bumps" are preferred to a continuous ring configuration because less friction is experienced after surmountable stop means 57 has been overcome and during the sliding action of insertion tube 50 through protective sleeve 41, permitting easy operation of tissue or mucus sampling device 40 in collection of a sample.

The cross-sectional distance between the outer surfaces of surmountable stop means 57 as shown in the figure at its widest portion is slightly larger than the inside diameter of protective sleeve 41, so that upon insertion of insertion tube 50 into protective sleeve 41, surmountable stop means 57 will come into contact with edge 43 of protective sleeve 41 and prevent easy further insertion into protective sleeve 41. For example, surmountable stop means 57 may have a diameter at its widest portion of about 0.217 inches while the inside diameter of protective sleeve 41 is about 0.210 inches. A slightly greater insertion force on handle member 65 will overcome the resistance provided by the contact of surmountable stop means 57 with edge 43 of protective sleeve 41, allowing insertion tube 50 to be fully inserted into protective sleeve 41 to the point where edge 43 of protective sleeve 41 contacts stop means 55.

As seen in FIG. 4, when surmountable stop means 57 is in contact with edge 43 of protective sleeve 41, tissue or mucus sampling member 60 remains inside protective sleeve 41. Optimally, tissue or mucus sampling member 60 is fully within protective sleeve 41, and may be located even further within protective sleeve 41 than shown by the figure by reducing the distance between tissue or mucus sampling member 50 and surmountable stop means 57.

FIG. 5 shows tissue or mucus sampling device 40 where surmountable stop means 57 has been overcome by additional insertion force at handle member 65, thereby fully engaging insertion tube 50 within protective sleeve 41. Tissue or mucus sampling member 60 protrudes at least partially from protective sleeve 41, enabling a sample to be taken.

FIG. 6 shows an alternative tissue or mucus sampling device configuration wherein insertion tube 70 is provided with scraper 71 as the tissue or mucus sampling member.

Tissue or mucus sampling device 40 is assembled by fitting tissue or mucus sampling member 60 onto insertion tube 50 and sliding insertion tube 50 into protective sleeve 41 until surmountable stop means 57 contacts edge 43 of protective sleeve 41. Tissue or mucus sampling device 40 will have been premeasured and manufactured so that when surmountable stop means 57 is in contact with edge 43 of protective sleeve 41, tissue or mucus sampling member 60 remains inside protective sleeve 41 to avoid contamination of tissue or mucus sampling member 60 with vaginal fluids or mucus.

Tissue or mucus sampling device 40 is then inserted into the vaginal cavity until tip 48 contacts the cervical os. Guard means 45 is then moved into contact with the vaginal orifice to prevent further insertion of tissue or mucus sampling device 40 into the vaginal cavity to avoid possible injury to the user. Of course, if tissue or mucus sampling device 40 has previously been used for collecting a cervical sample, guard means 45 would already be in the desired position on protective sleeve 41. Insertion sleeve 50 is then pushed forwardly into protective sleeve 41 by handle member 65 until tissue or mucus sampling member 60 is in the predetermined "in use" position shown in FIG. 5. Handle member 65 can then be gently rotated to thus collect a mucus sample. Insertion tube 50 is retracted a short distance, at least beyond surmountable stop means 57, and tissue or mucus sampling device 40 is then withdrawn. Protective sleeve 41 shields insertion tube 50 and particularly tissue or mucus sampling member 60 during the entire insertion and removal process. Insertion tube 50 is completely withdrawn from protective sleeve 41 and the collected mucus sample is available for further processing for examination and testing.

After each use, device 40 is completely cleaned by washing with soap and water and is ready for reuse. Tissue or mucus sampling member 60, if the mucus collecting swab was used, is discarded; if a scraper form was used, it is also washed for reuse.

When conducting in vivo testing of ovulation prediction, swabs made of hydrophilic polymer or swabs with hydrophilic polymer coated surfaces provide better cervical mucus sampling than other types of materials. The best forms include an open cell foam structure and surfaces with amny capillary openings. Their surfaces provide good adsorption of the mucus sample, but also free release of the sample during the subsequent extraction. To illustrate this, the following experiment was performed:

0.15 ml samples of cervical mucus were dropped onto pads of the fibrous test materials. After a one minute delay to allow the mucus to be completely absorbed, the fibrous test materials were extracted in an aqueous solution consisting of a buffer, and a reactive mixture that gave a colorimetric reaction in the presence of an enzyme in the mucus. The color change could be read quantitatively after two minutes as an optical absorbance at 470 nm, and is indicative of the quantity of mucus extracted. As a control, a 0.15 ml sample was added directly to a sample of the reactive mixture and its absorbance read after two minutes at 470 nm.

The ratio below gives the sample-release efficiency of the swab, i.e., $$\% \text{ efficiency} = \frac{A \; 470 \text{ nm}}{B \; 470 \text{ nm}} \times 100\%$$

where $A$: optical absorption of solution after test swab was coated with fixed amount of cervical mucus and was subsequently extracted and reacted;

and $B$: optical absorption of solution with fixed amount of cervical mucus added directly to the buffer reaction mixture.

| Material Description | Sample-Release Efficiency % |
|---|---|
| Thermal bonded polyester web (3M) | 106 |
| Polyacrylonitrile web (Du Pont Orlon) | 99 |
| Polyurethane open cell foam (Scott Foam Division of Scott Paper Company) | 92–87 |
| Rayon web (3M) | 82 |
| Hydrophilic polyurethane foam (Polyurethane prepolymer derived from toluene diisocyanate) (3M) | 74 |
| Cotton, Polypropylene, Polyester bicomponent web (3M) | 74–61 |
| Rayon fiber (PurFybr, Inc.) | 67 |
| Calcium alginate fiber, Polyester fiber (PurFybr, Inc.) | 57–47 |
| Polyethylene closed cell foam (Scott Foam Division of Scott Paper Company) | 33 |

For the ovulation prediction test, the preferred test swab material is the polyurethane open cell foam, because of its availablity, low cost, low toxicity, ease of manufacturing and the described release efficiency.

What is claimed is:

1. A tissue or mucus sampling device for obtaining a tissue or mucus sample from the cervical os or the vaginal fornix comprising at one-piece elongate, cylindrical outer protective sleeve terminating in a tip, positionable guard means on said protective sleeve for limiting the insertion depth of said device into the vaginal cavity, an elongate, cylindrical insertion tube having a first end and a second end telescopically fitting within said protective sleeve, surmountable stop means on said insertion tube for temporarily inhibiting said first end of said insertion tube from protruding through said protective sleeve, stop means on said insertion tube for permanently limiting the extent of protrusion of said tube beyond said sleeve, a tissue or mucus sampling member on said first end of said insertion tube and a handle member affixed to said second end of said insertion tube for manipulating said tube.

2. A tissue or mucus sampling device according to claim 1 wherein said tip of said protective sleeve has a reduced diameter orifice.

3. A tissue or mucus sampling device according to claim 1 wherein said protective sleeve is semi-rigid and is selected from the group consisting of polyvinyl chloride, polypropylene, polyethylene, polyethylene terephthalate, polycarbonate, Teflon and Nylon.

4. A tissue or mucus sampling device according to claim 3 wherein said protective sleeve is curved at an angle of from 15° to 45° from the horizontal.

5. A tissue or mucus sampling device according to claim 4 wherein said angle is 22.5° and occurs at a point which is located about one fifth of the total length of said protective sleeve.

6. A tissue or mucus sampling device according to claim 1 wherein said insertion tube is semi-rigid and is formed of a material selected from the group consisting of polyvinyl chloride, polypropylene, polyethylene, polyethylene terephthalate, polycarbonate, polystyrene, Teflon and Nylon.

7. A tissue or mucus sampling device according to claim 1 wherein said tissue or mucus sampling member comprises an elongate semi-rigid rod having a covering at one end thereof of a flexible, soft, resilient fibrous material selected from the group consisting of cotton, rayon, polyester and calcium alginate.

8. A tissue or mucus sampling device according to claim 1 wherein tissue or mucus sampling member comprises a flexible foam pad directly affixed to said insertion tube.

9. A tissue or mucus sampling device according to claim 1 wherein said tissue or mucus sampling member comprises an elongate semi-rigid rod having a covering at one end thereof of a flexible foam pad.

10. A tissue or mucus sampling device according to claim 9 wherein the flexible foam pad is a polyurethane open cell foam pad.

11. A tissue or mucus sampling device according to claim 1 wherein said tissue or mucus sampling member comprises an elongate semi-rigid rod having a scraper member affixed to one end thereof.

12. A tissue or mucus sampling device according to claim 1 wherein said surmountable stop means comprises one or more protruberances on said insertion tube such that the widest diameter of said insertion tube is at the point of said protruberance or protruberances and is slightly wider than the inner diameter of said protective sleeve.

13. A tissue or mucus sampling device according to claim 1 wherein said tissue or mucus sampling member is made of a hydrophilic polymeric material.

14. A tissue or mucus sampling device according to claim 1 wherein said tissue or mucus sampling member has a hydrophilic polymeric surface.

* * * * *

UNITED STATES PATENT AND TRADEMARK OFFICE
CERTIFICATE OF CORRECTION

PATENT NO. : 4,877,037

DATED : October 31, 1989

INVENTOR(S) : Su-sen Ko and Dan L. Fanselow

It is certified that error appears in the above-identified patent and that said Letters Patent is hereby corrected as shown below:

Col. 1, line 19, "the" should read -- to --.

Col. 2, line 68, "top" should read -- tip --.

Col. 4, line 65, "shon" should read -- shown --.

Col. 6, line 15, "50" should read -- 60 --.

Col. 7, line 4, "amny" should read -- many --.

Col. 7, line 62, "at" should read -- a --.

Col. 8, line 39, after "wherein" insert -- said --.

Signed and Sealed this

Thirtieth Day of April, 1991

*Attest:*

HARRY F. MANBECK, JR.

*Attesting Officer*   Commissioner of Patents and Trademarks